United States Patent [19]

Lee

[11] Patent Number: 4,816,062

[45] Date of Patent: Mar. 28, 1989

[54] HERBICIDAL COMPOSITIONS AND METHOD CONTAINING 3,5-DICARBOXYLIC ACID ESTERS OF 2,6-BIS-(FLUORO-ALKYL) TETRAHYDROPYRANS

[75] Inventor: Len F. Lee, St. Charles, Mo.

[73] Assignee: Monsanto Company, St. Louis, Mo.

[21] Appl. No.: 869,509

[22] Filed: Jun. 2, 1986

Related U.S. Application Data

[60] Division of Ser. No. 602,023, Apr. 24, 1984, Pat. No. 4,618,679, which is a continuation-in-part of Ser. No. 522,271, Aug. 11, 1983, abandoned.

[51] Int. Cl.$^4$ .................. A01N 43/16; C07D 309/10; C07D 407/04; C07D 409/04
[52] U.S. Cl. ............................ 71/88; 71/90; 549/60; 549/414; 549/417
[58] Field of Search .................. 549/417, 60, 414; 71/88, 90

[56] References Cited

PUBLICATIONS

A. Dey, et al., *J. Org. Chem.*, 30, 3237–3239 (1965).

*Primary Examiner*—Richard A. Schwartz
*Attorney, Agent, or Firm*—James C. 36Bolding

[57] ABSTRACT

The disclosure herein pertains to herbicidal methods and compositions containing 3,5-dicarboxylic acid esters of 2,6-bis-(fluoroalkyl) tetrahydropyrans and piperidines which may be substituted in the 4-position by certain alkyl, phenyalkyl, phenyl, alkoxyalkyl, alkylthioalkyl, cycloalkyl, and heterocyclic radicals wherein the hetero atom is oxygen and sulfur and to a process for the preparation thereof. These compounds are useful as pre-emergent herbicides.

23 Claims, No Drawings

HERBICIDAL COMPOSITIONS AND METHOD CONTAINING 3,5-DICARBOXYLIC ACID ESTERS OF 2,6-BIS-(FLUORO-ALKYL) TETRAHYDROPYRANS

This is a division of application Ser. No. 602,023, filed Apr. 24, 1984, now U.S. Pat. No. 4,618,679, which is a continuation-in-part of application Ser. No. 522,271, filed Aug. 11, 1983, now abandoned.

BACKGROUND OF THE INVENTION

1. Field of the Invention

The invention herein pertains to the field of herbicides. More particularly, the field of this invention pertains to the use of bis-(3,5-dicarboxylic) esters of tetrahydropyrans and piperidines as preemergent herbicides.

2. Description of the Prior Art

Bis-(2,6-trifluoromethyl)-3,5-dicarboxylic acid esters of tetrahydropyrans and piperidines are known. Baldev Singh et al published a report of their investigation in the Journal of Heterocyclic Chemistry, Vol. 17, 1109 (1980) wherein they describe the reaction of ethyl 4,4,4-trifluoroacetoacetate with arylaldehydes and aqueous ammonia in ethanol. They discovered that such a reaction, previously reported by Balicki et al, Chem Abstracts, Vol. 82, 72739P (1975) produced diethyl 4-aryl-2,6-dihydroxy-2,6-bis-(trifluoromethyl)-3,5-piperidinedicarboxylates instead of diethyl 4-aryl-1,4-dihydro-2,6-bis(trifluoromethyl)-3,5-pyridinedicarboxylates. Stereo isomers of the reported piperidinedicarboxylates was also reported as being uncertain. No use was given for the compounds.

The Journal of Organic Chemistry, Vol. 30, pages 3237–3239, September, 1965, contains a report by Dey et al on the synthesis of fluorine-containing tetrahydropyrans. By the process for reacting ethyl trifluoroacetoacetate with various aliphatic and aromatic aldehydes using the usual Knoevenagel conditions provided various 4-substituted compounds. Condensation of ethyl trifluoroacetoacetate with aldehydes was carried out in the presence of both piperidine and potassium fluoride in two different methods to provide the compounds of interest. Compounds substituted in the 4-position by methyl, ethyl, phenyl, p-fluorophenyl and p-methoxyphenyl were reported on the 3,5-dicarbethoxy-2,6-dihydroxy-2,6-bis-(trifluoromethyl) tetrahydropyran molecule. No use was given for the compound, nor are branched-chain alkyl substituents disclosed in the 4-position.

In U.S. Pat. No. 3,700,695 to Carr et al, there is disclosed compounds having the following general formula

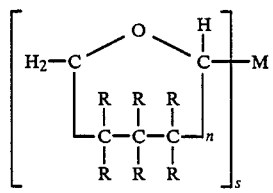

wherein n is from 0 to 1, wherein one of the R's is selected from the group consisting of fluorine, alkyl, cycloalkyl, aryl, perfluoroalkyl, perfluorocycloalkyl, and perfluoroaryl, wherein another one of the R's may be selected from the group consisting of alkyl and perfluoroalkyl, wherein the remaining R's are selected from the group consisting of hydrogen and fluorine, provided that at least one of the R's contains fluorine or is fluorine, s is a number from 1 to 3 inclusive, and M is substance selected from the group consisting of fluorine, chlorine, bromine, iodine, cyano, alkylcarbonyloxy, arylcarbonyloxy, cycloalkylcarbonyloxy, alkylsulfonyloxy, cycloalkylsulfonyloxy, arylsulfonyloxy, phosphinylidynetrioxy, phosphinidynetrioxy, alkoxyphosphinidenedioxy, dialkoxyphosphinoxy, aryloxyphosphinidenedioxy, diaryloxyphosphinoxy, alkylphosphinylidenedioxy, arylphosphinylidenedioxy, sulfonyl and sulfinyl. The preparation of these compounds and their uses in improving the clarity of plastic films and as herbicides are also described. As is indicated by the above formula, fluorine substitution in these compounds occurs on the ring directly or the ring may be substituted by perfluoroalkyl radicals. Certain of these compounds are reported to have herbicidal activity while the majority of compounds were utilized in polyvinyl chloride films as clarifiers. The herbicidally-active compounds generally were ring substituted fluorine-containing compounds having a carbonyloxy or sulfonyloxy radical in the 2-position of the pyran ring. Pre-emergent herbicidal activity of such compounds is noted with respect to rice, millet and cucumber.

While, as will be apparent from the above, the compositions of this invention have been noted in the prior art, none of the prior art discloses or suggests the utility of the dicarboxylate esters as preemergent herbicides nor is there disclosed the novel process of the present invention for preparing such compounds.

SUMMARY OF THE INVENTION

The present invention relates to herbicidally active compounds, a novel process for preparing them, herbicidal compositions containing these compounds and herbicidal methods of use of said compositions in agriculture.

The herbicidal compounds of this invention are characterized by the formula

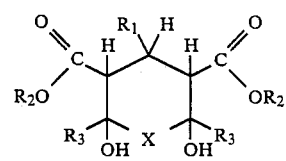

wherein X is selected from O or NH and, when X is O, $R_1$ is selected from the group consisting of hydrogen, lower alkyl, phenyl, phenylmethyl, alkoxyalkyl, alkylthioalkyl, cycloalkyl, cycloalkanylalkyl, and heterocyclic radicals having 3 to 6 members in the ring in which 1 to 3 members is a hetero atom selected from O or S; when X is NH, $R_1$ is selected from the group consisting of lower alkyl, phenyl, alkoxyalkyl, alkylthioalkyl, cycloalkyl, heterocyclic radicals and lower alkyl-substituted heterocyclic radicals having 3 to 6 members in the ring of which 1 to 3 members are selected from O and S; $R_2$ is a $C_{1-4}$ alkyl radical and $R_3$ represents a $C_{1-4}$ fluoroalkyl radical provided that when X is O and $R_3$ is pentafluoroethyl, $R_1$ cannot be hydrogen or 1-methylethyl and further provided that when X is NH and $R_1$ is furyl, $R_3$ cannot be pentafluoroethyl and when X is NH and $R_3$ is trifluoromethyl $R_1$ cannot be methyl or 1-ethylpropyl.

The term "lower alkyl" is intended to mean both straight and branched chain $C_{1-5}$ alkyl groups. By "branched chain" alkyl groups is meant an alkyl group substituted with one or more additional alkyl groups so that the total number of carbon atoms does not exceed 5. These include, but are not limited to, radicals such as 2-methylpropyl, 2,2-dimethylpropyl, 2-methylbutyl, and 3-methylbutyl.

Preferred compounds of this invention are those wherein $R_1$ is alkyl, $C_{1-5}$ and within that group of compounds more preferred compounds are those wherein $R_1$ is alkyl $C_{2-4}$, with compounds in which $R_1$ is a $C_{3-4}$ branched chain alkyl being most preferred. Typical $R_1$ and $R_2$ alkyl radicals include methyl, ethyl, 1-methylethyl, n-propyl, n-butyl, 2-methylpropyl, 1-ethylpropyl, and n-pentyl.

Typical $R_1$ heterocyclic radicals include, 2-thienyl, 3-thienyl, 2-furyl, 3-furyl, and substituted furyl wherein the substituent is lower alkyl.

Typical $R_3$ $C_{1-4}$ fluoroalkyl radicals include but are not limited to trifluoromethyl, difluoromethyl, monofluoromethyl, chlorodifluoromethyl, dichlorofluoromethyl, and pentafluoroethyl radicals.

DETAILED DESCRIPTION OF THE INVENTION

The piperidine compounds of this invention are obtainable in two stereo isomeric forms generally termed the "trans-" and the "cis-" isomers. In accordance with this invention the herbicidal utility of the above described piperidine compounds have been observed in both isomeric forms and in admixture. The disclosure and claims herein encompass both isomeric forms and mixtures thereof.

As confirmed by single crystal X-ray crystallography, the isomeric structures are represented by the formula wherein (a) is cis and (b) is trans.

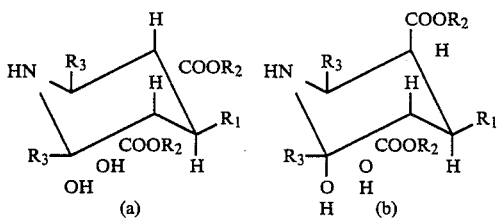

The pyrans of this invention are prepared in accordance with the following reactions:

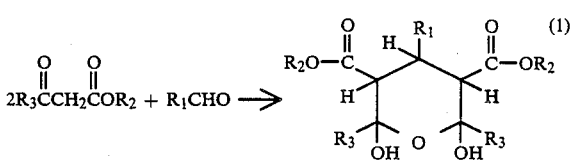

From the above, it is seen that the pyran is produced by the reaction of an aldehyde with an appropriate 3-ketoester in the presence of either piperidine or potassium fluoride in catalytic amounts. When the reaction between the aldehyde and the 3-ketoester is performed in the presence of aqueous ammonia, piperidine compounds are provided as taught by Singh et al referred to above according to the following reaction:

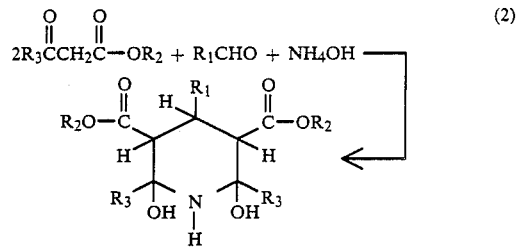

The above reaction (2) typically utilizes a suitable vehicle such as ethanol and is usually conducted at reflux temperature for a period on the order of about three to five hours. The above reaction (2) is generally inefficient because of low yield of the desired compounds as compared to the process of this invention more fully set forth below in Example 16 and 17.

Example 1

Preparation of 2H-Pyran-3,5-Dicarboxylic Acid, Tetrahydro, 2,6-Dihydroxy-4-(1-Ethylpropyl)-2, 6-bis(Trifluoromethyl)-, Diethyl Ester.

To a 1 liter flask is charged 50 g (0.4992 mol) of 2-ethylbutyraldehyde and 183.81 g (0.9984 mol) of ethyl trifluoroacetoacetate. To this mixture 3–5 ml of piperidine (catalyst) is slowly added by pipette. Stirring is continued for 24 hours after which the mixture is left standing for 5 days before crystallizing. Solid product yields 66.45 g (25%); mp 105°–110° C. The product is identified as the trans isomer.

Anal. Calc'd. for $C_{18}H_{26}F_6O_7$: C, 46.15; H, 5.55; Found: C, 46.23; H, 5.66.

EXAMPLE 2

Preparation of 2H-Pyran-3,5-Dicarboxylic Acid, Tetrahydro-2,6-Dihydroxy-4-(2-Methylpropyl)-2,6-bis-(Trifluoromethyl)-, Diethyl Ester To a 1-liter flask is charged 50 g (0.5805 mol) of isovaleraldehyde and 213.75 g (1.1610 mol) of ethyl trifluoroacetoacetate. To this mixture is slowly added 3–4 ml of piperidine (catalyst) by pipette. The mixture begins to exotherm vigorously and the flask is fitted with a condenser and nitrogen line. After stirring for 2 hours, the mixture crystallizes. Trituration with n-hexane yields 170.37 g (64%) of 2H-pyran-3,5-dicarboxylic acid, tetrahydro-2,6dihydroxy-4-(2-methylpropyl)-2, 6-bis(trifluoromethyl)-,diethyl ester; mp 87°–90° C. This product is identified as the trans isomer.

Anal. Calc'd. for $C_{17}H_{24}F_6O_7$: C; 44.93; H, 5.28; Found: C, 45.02; H, 5.20.

EXAMPLE 3

Preparation of 2H-Pyran-3,5-Dicarboxylic Acid, Tetrahydro-2,6-Dihydroxy-4-(Phenylmethyl)-2,6-bis-(Trifluoromethyl)-, Diethyl Ester.

A 500 ml flask is charged with 50 g (0.4162 mol) of phenylacetaldehyde and 153.28 g (0.8325 mol) of ethyl trifluoroacetoacetate and placed in an ice water bath. To the cooled, stirred mixture, 3–4 ml of piperidine is slowly added by pipette. After stirring for 18 hours, crystals are filtered and triturated in hot hexane to yield 34.92 g (18%) of 2H-Pyran-3,5-dicarboxylic acid, tetrahydro-2,6-dihydroxy-4-(phenylmethyl)-2,6-bis(trifluoromethyl)-, diethyl ester; mp 120°–125° C.

Anal. Calc'd. for $C_{20}H_{22}F_6O_7$: C, 49.07; H, 4.70; Found: C, 49.79; H, 4.41.

EXAMPLE 4

Preparation of 2H-Pyran-3,5-Dicarboxylic Acid, Tetrahydro-2,6-Dihydroxy-4-Pentyl-2,6-bis (Trifluoromethyl)-, Diethyl Ester To a single necked, 500 ml flask is charged 37.5 g (0.375 mol) of hexanal and 138.08 g (0.75 mol) of ethyl trifluoroacetoacetate. After stirring the mixture, approximately 3–5 ml of piperidine (catalyst) are slowly added by pipette. The mixture is stirred for 18 hours and the resulting solid is stirred in n-hexane and filtered to give 112.80 g (65%) of a white solid; mp 99°–104° C. This product is a mixture of cis and trans isomers in a ratio of about 1:3.

Anal. Calc'd. for $C_{18}H_{23}F_6O_7$: C, 46.45; H, 4.94; Found: C, 46.34; H, 5.05.

EXAMPLE 5

Preparation of 2H-Pyran-3,5-Dicarboxylic Acid, 4-Butyl-Tetrahydro-2,6-Dihydroxy-2,6-bis(Trifluoromethyl)-, Diethyl Ester To a single necked 500 ml flask is charged 30.14 g (0.35 mol) of valeraldehyde and 128.87 g (0.70 mol) of ethyl trifluoroacetoacetate. After stirring the mixture, 3–4 ml of piperidine (catalyst) are added slowly by pipette. The mixture begins to exotherm. After stirring for 18 hours, the mixture is diluted with n-hexane and set on dry ice to crystallize. White crystals result providing a yield of 14.10 g (9%) of product having a melting point of 6°–51° C. This product is a mixture of cis and trans isomers in a ratio of about 3:1, respectively.

Anal. Calc'd. for $C_{17}H_{24}F_6O_7$: C, 44.93; H, 5.28; Found: C, 45.16; H, 5.27.

EXAMPLE 6

Preparation of 2H-Pyran-3,5-Dicarboxylic Acid Tetrahydro-2,6-Dihydroxy-4-Ethyl-2,6-bis(trifluoromethyl)-, Diethyl Ester A 500 ml flask is charged with 17.42 g (0.3 mol) of propionaldehyde, 110.46 g (0.6 mol) of ethyl trifluoroacetoacetate and 1–2 ml of piperidine. The mixture becomes so exothermic upon heating that the flask is placed quickly in a water bath. Crystallization occurs within 3–5 minutes. The crystals are stirred with n-hexane and filtered to give 68.91 g (53.92%) of product; mp 123°–127° C. This product is the cis isomer.

Anal. Calc'd. for $C_{15}H_{20}F_6O_7$: C, 42.25; H, 4.69; Found: C, 42.41; H, 4.72.

EXAMPLE 7

Preparation of 2H-Pyran-3,5-Dicarboxylic Acid-4-(2-Furyl)-Tetrahydro-2,6-Dihydroxy-2,6-bis(-pentafluoroethyl)-Diethyl Ester A 500 ml single-necked flask is charged with 25 g (0.2601 mol) of 2-furaldehyde and 121.7 g (0.5202 mol) of ethyl pentafluoropropionyl acetate. To this mixture is added 1 ml of piperidine (catalyst) by pipette. The mixture is stirred 18 hours and triturated with n-hexane, filtered and recrystallized from methyl cyclohexane to give 92.50 g (63%) of solid; mp 114°–118° C.

Anal. Calc'd. for $C_{19}H_{18}F_{10}O_8$: C, 40.42; H, 3.19; Found: C, 40.56; H, 3.22.

EXAMPLE 8

Preparation of 2H-Pyran-3,5-Dicarboxylic Acid, Tetrahydro-2,6-Dihydroxy-4-(1-Methylethyl)-2,6-bis(-Trifluoromethyl)-Diethyl Ester A 500 ml round bottomed flask is charged with 20 g (0.2773 mol) of isobutyraldehyde and 102.12 g (0.5547 mol) of ethyl trifluoroacetoacetate. A magnetic stirrer is added and the mixture stirred while 5–10 drops of piperidine are added by pipette. The reaction mixture is placed under nitrogen and stirred for 18 hours. The viscous liquid is pumped down under vacuum for approximately an hour. The flask is cooled in an ice bath. The resulting crystals are triturated in n-hexane and filtered to give 22.42 g (18.37%) of product; mp 88°–98° C. This product is a 1:1 mixture of cis and trans isomers.

Anal. Calc'd. for $C_{16}H_{22}F_6O_7$: C, 43.63; H, 5.01; Found: C, 43.73; H, 5.05.

EXAMPLE 9

Preparation of 2H-Pyran-3,5-Dicarboxylic Acid, Tetrahydro-2,6-Dihydroxy-4-Propyl-2,6-bis (Trifluoromethyl)-Diethyl Ester.

A 500 ml single-necked flask is charged with 20 g (0.2773 mol) of butyraldehyde, 102.12 g (0.5547 mol) of ethyl trifluoroacetoacetate and approximately 150 ml of ethanol. To this is added 3 g (0.0516 mol) of potassium fluoride. The mixture is stirred at room temperature for 18 hours. The material is concentrated and diluted with ethyl ether. The organics are washed with water, dried and concentrated to give a white powder. The crude product is recrystallized from hot methylcyclohexane to give 13 g of product (10.65%); mp 128°–132° C. This product is a mixture of cis and trans isomers in a ratio of 1:1, respectively.

Anal. Calc'd for $C_{16}H_{22}F_6O_7$: C, 43.63; H, 5.00; Found: C, 43.88; H, 5.04.

EXAMPLE 10

2H-Pyran-3,5-Dicarboxylic Acid, Tetrahydro-4-Ethyl-2,6-Dihydroxy-2,6-bis(Pentafluoroethyl)-, Diethyl Ester To a mixture of 114 g (0.5 mol) of ethyl pentafluoropropionylacetate and 15 g (0.25 mol) of propionaldehyde are added a few drops of piperidine. The reaction mixture is allowed to react for 117 hours, triturated with hexane, and filtered. The solid material is recrystallized from hexane to give 45.2 g of first crop, mp 87°–92° C., 16.8 g of second crop, mp 81°–86° C., and 14 g of third crop, mp 83°–86° C. Total yield is 76 g of product.

Anal. Calc'd. for $C_{17}H_{20}F_{10}O_7$: C, 38.79; H, 3.83; Found: C, 39.13; H, 3.87.

EXAMPLE 11

2H-Pyran-3,5-Dicarboxylic Acid, Tetrahydro-2,6-Dihydroxy-4-Phenyl-2,6-bis(Trifluoromethyl)Diethyl Ester A mixture of 36.8 g (0.20 mol) of ethyl trifluoroacetoacetate, 10.6 g (0.10 mol) of benzaldehyde and 0.1 g of piperidine are stirred for hours. The reaction mixture is crystallized from hexane at low temperature to give 8.54 g (18%) of white needles, mp 104°–110° C. This material is recrystallized from ether-hexane to give 4.07 g (8.6%) of product, mp 128°–136.5° C. This product is the cis isomer. Additional 31.3 g (66%) of product is obtained by concentration of the mother liquor.

Anal. Calc'd. for $C_{19}H_{20}F_6O_7$: C, 48.11; H, 4.25; Found: C, 47.68; H, 4.07

EXAMPLE 12

2H-pyran-3,5-dicarboxylic acid, tetrahydro 2,6-dihydroxy-2,6-bis(trifluoromethyl)-,diethyl ester To a well stirred cold (10° C.) mixture of 92.0 g (0.5 mol) of ethyl trifluoroacetoacetate and 20.07 g (0.25 mol) of 37.5% formaldehyde is added a solution of 0.25 g piperidine in 8 ml of ethanol. The reaction mixture is stirred at 20°–25° C. for 40 minutes. Additional 1.6 g of piperidine is added to the reaction mixture. The temperature of the reaction mixture rises spontaneously to 60° C. After stirring for 1 hour, the reaction mixture is filtered and washed successively with water and hexane to give 52.6 g (52.8%) of product, mp 84°–104° C. Additional 20.8 g (20.8%) of product is obtained from the filtrate after one week.

Anal. Calc'd. for $C_{13}H_{16}F_6O_7$: C, 39.20; H, 4.05; Found: C, 39.44; H, 4.00

Additional compounds of this invention were prepared using the appropriate aldehydes and 3-ketoesters by a procedure similar to Example 6 above and are listed in Table I.

important to distinguish the catalyst which is the compound piperidine itself from the substituted piperidine compound produced by the reaction of the aldehyde and 3-ketoester reactants in the process. The improved process of this invention can be performed in a sequential manner whereby the crude product of the initial reaction between the aldehyde and 3-ketoester is isolated and admitted to a second reaction vessel wherein the product is treated with gaseous ammonia to provide the desired piperidine compound. Alternatively, the crude reaction product of the initial reaction between the 3-ketoester and aldehyde in the presence of a catalytic amount of piperidine can be immediately treated in the same reaction vessel with gaseous ammonia and the desired piperidine compound isolated from the reaction mixture.

It has also been observed that the improved process of this invention provides two stereo isomers of the substituted piperidine compounds. In the case of the trans isomer, the two carboxylate groups are in different planes, whereas, in the cis isomer, both carboxylate groups lie in the same geometric plane.

Accordingly, the reaction of an aldehyde and 3-ketoester is performed in the presence of a small, catalytic amount of piperidine, in a suitable reaction medium. After completion of the initial reaction, gaseous ammo-

TABLE 1

$$\underset{R_2O}{\overset{O}{\underset{\|}{C}}} \overset{R_1\ H}{\underset{R_3\ OH}{\diagup}} \overset{H}{\underset{X}{\cdot}} \overset{}{\underset{OH\ R_3}{\diagdown}} \overset{O}{\underset{\|}{C}} OR_2$$

| | | | | Analysis | | | | | Isomer | |
| | | | | C | | H | | Melting | % Ratio | |
| Example Number | $R_1$ | $R_2$ | $R_3$ | X | Calc'd | Found | Calc'd | Found | Point °C. | Cis | Trans |
|---|---|---|---|---|---|---|---|---|---|---|---|
| 13 | —CH$_2$CH(CH$_3$)$_2$ | —CH$_3$ | CF$_3$ | 0 | 42.26 | 42.54 | 4.73 | 4.77 | 83–87 | 83 | 17 |
| 14 | —CH$_3$ | —CH$_2$CH$_3$ | CF$_2$CF$_3$ | 0 | 37.50 | 37.70 | 3.51 | 3.57 | 96–104 | | |
| 15 | —⟨cyclohexyl⟩ | —CH$_2$CH$_3$ | CF$_2$CF$_3$ | 0 | | | | | | | |
| 16 | —⟨cyclohexyl⟩ | —CH$_2$CH$_3$ | CF$_3$ | 0 | 47.60 | 47.38 | 5.26 | 5.63 | 100–103 | | |
| 17 | —⟨cyclopropyl⟩ | —CH$_2$CH$_3$ | CF$_3$ | 0 | 43.84 | 43.93 | 4.60 | 4.52 | 98–101 | | |
| 18 | —CH$_2$OCH$_2$—⟨phenyl⟩ | —CH$_2$CH$_3$ | CF$_3$ | 0 | 49.03 | 49.45 | 4.71 | 4.71 | 90–93 | 100 | — |
| 19 | —CH$_2$OCH$_3$ | —CH$_2$CH$_3$ | CF$_3$ | 0 | 40.73 | 40.69 | 4.56 | 4.72 | 77.5–81 | 89 | 11 |

There is provided, in accordance with this invention, an improved process for preparing dihydroxypiperidine compounds of this invention, the improvement comprising reacting said aldehyde and 3-ketoester in the presence of piperidine as a catalyst and passing gaseous ammonia through the reaction mixture and allowing the crude product to react therewith to produce the desired piperidine compounds. In this improved process, it is nia is introduced into the reaction mixture and the mixture allowed to react therewith to provide a relatively high yield of piperidine compound which is easily isolated by fractional crystallization within an appropriate solvent. The reaction is carried out generally at reflux temperature, but temperatures of 40°–80° C. are normally adequate. The amount of gaseous ammonia is generally in the range of 2 to 10 mols of ammonia per mol of aldehyde desired to be converted.

In one embodiment of the novel process of this invention, the aldehyde and 3-ketoester are allowed to react, usually at reflux temperature for a period of about one hour after which a small amount of aldehyde is added to the reaction mixture and further reflux continued. The reaction mixture is then treated, without additional heating, with ammonia gas by passing the gas through the reaction mixture over a suitable period of time. The product is normally obtained as a precipitate from the mixture. Additionally, improved yield is obtained by utilizing tetrahydrofuran as the reaction medium in place of the prior art organic solvent.

To illustrate the improvement, the following Example 20 is illustrative of the prior art and can be compared to Example 21.

EXAMPLE 20

(Prior Art)

Piperidine-3,5-Dicarboxylic Acid, 2,6-Dihydroxy-4-Phenyl-2,6-bis(Trifluoromethyl)-,3,5-Diethyl Ester To a mixture of 36.8 g (0.2 mol) of ethyl trifluoroacetoacetate, and 10.6 g of benzaldehyde is added 10 ml of 58% ammonium hydroxide followed by 20 ml of ethanol. The reaction mixture is held at reflux for 18 hours and poured into ice water. The oily precipitate is extracted into ether. The ether solution is dried and concentrated in vacuo. The residual oil (43.6 g) is crystallized from petroleum ether to give 12.73 g of solid, mp 88°–98° C. This material is stirred with 1.31 g of 58% ammonium hydroxide and 60 ml of ethanol for 2 hours and concentrated in vacuo. The residual solid is recrystallized from hot hexane to give 4.71 g (10% based on ethyl trifluoroacetoacetate) of product, mp 99°–100° C.

Anal. Calc'd. for $C_{19}H_{21}F_6N_1O_6$: C, 48.21; H, 4.27; N, 2.96; Found: C, 47.96; H, 4.05; N, 2.79.

EXAMPLE 21

Piperidine-3,5-Dicarboxylic Acid, 2,6-Dihydroxy-4-Phenyl-2,6-bis(Trifluoromethyl)-, Diethyl Ester To provide a comparison with the prior art, the following procedure, in accordance with the process of this invention, provides the desired piperidine by treating the initial, crude reaction mixture of the acetate and aldehyde with gaseous ammonia.

Through a refluxing mixture of 30.3 g (0.0638 mol) of the isolated product of Example 11, and 100 ml of tetrahydrofuran is passed 82 g (5.4 mol) of ammonia in 4 hours. The reaction mixture is analyzed by $^{19}F$ nmr and is found to contain a 5:1 mixture of the cis and trans stereo isomers, respectively. The reaction mixture is concentrated and the residue is recrystallized from petroleum ether to give 20.0 g (66%) of the cis isomer, mp 97°–98° C. The yield of the cis isomer by this reaction is 51% based on the ethyl trifluoroacetoccetate starting material of Example 11. The filtrate is concentrated to give a residue containing both cis and trans isomers.

EXAMPLE 22

To provide further comparison to the prior art, there is provided in this Example 22 three preparations of the same compound. In 22(a) there is provided an example of the prior art wherein a relatively high proportion of by-product is obtained. In 22(b) the prior art reaction is repeated with the exception that tetrahydrofuran replaces ethanol as the reaction medium which results in an improved yield of the desired product. The process of this invention is provided in 22(c) indicating a further increase in yield of the desired products.

(a)

Reaction of Ethyl Trifluoroacetoacetate With Propionaldehyde and Ammonium Hydroxide in Ethanol To a 4 liter four-necked flask if charged 368 g (2.0 mol) of ethyl trifluoroacetoacetate, 58.1 g (1.0 mol) of propionaldehyde, 400 ml of ethanol and 91 g (1.50 mol) of 58% ammonium hydroxide. The mixture is held at reflux for 1 hour and analyzed by $^{19}F$ nmr (using $CCl_3F$ as internal standard) which indicates the reaction mixture contains 31% of cis isomer (δ-85.09) of diethyl 2,6-dihydroxy-4-ethyl-2,6-bis-(trifluoromethyl)-3,5-piperidinedicarboxylate, 13% of its trans isomer (δ-84.04 and δ-85.15), 8% of cis isomer of the product of Example 6 (δ-86.69), 27% of ammonium salt of ethyl trifluoroacetoacetate (δ-76.25), 10% of ethyl 3amino-4, 4, 4,-trifluorocrotonate (δ-72.65), and 6% and 2% of unknown material (δ-86.19 and δ-83.73).

The reaction mixture is held at reflux for an additional 3 hours. The $^{19}F$ nmr indicates the only major change in the ratio of products is an increase of ethyl 3-amino-4,4,4-trifluorocrotonate (to 30%) and a decrease of ammonium salt of ethyl trifluoroacetoacetate. The reaction mixture is cooled in a dry ice-acetone bath, filtered and washed with water to give 90.0 g (21%) of a solid, m.p. 119°–130° C., which is mainly cis isomer (17a).

Anal. Calc'd. for $C_{14}H_{19}F_6N_1O_6$: C, 42.35; H, 4.94; N, 3.29; Found: C, 42.48; H, 5.00; N, 3.33.

(b)

Reaction of Ethyl Trifluoroacetoacetate With Propionaldehyde Follwed by Treatment of the Crude Product With Ammonium Hydroxide in Tetrahydrofuran To a mixture of 36.8 g (0.20 mol) of ethyl trifluoroacetoacetate and 5.8 g (0.10 mol) of propionaldehyde is added three drops of piperidine. The reaction mixture is exothermic and the temperature of the reaction mixture reaches 35° C. After 1 hour stirring, the reaction mixture is analyzed by $^{19}F$ nmr (in THF) which indicates the reaction mixture contains 32% of ethyl trifluoroacetoacetate hydrate (δ-87.43), 46% of an isomeric mixture of 2,6-bis-(trifluoromethyl)-4-ethyl-6-hydroxy-5,6-dihydropyran-3,5-dicarboxylic acid diethyl ester (a set of doublets at −69.02, −69.87, and −70.10 and a set of singlets at −84.20, −84.36, and −84.52), 11% of ethyl trifluoroacetoacetate (δ-75.65 and −82.69), 4% and 5% of two unidentified materials (δ-73.93 and −72.45). The above mixture is treated with 11.4 g (0.188 mol) of 58% aqueous ammonium hydroxide and stirred for 1.5 hours. The reaction mixture is analyzed by $^{19}F$ nmr to contain 56% of a 1:1 mixture of cis 2,6-bis-(trifluoromethyl)-2,6-dihydroxy-4-ethyl-3,5-piperidinedicarboxylic acid diethyl ester, and its trans isomer. The remainder is mainly ammonium salt of ethyl trifluoroacetoacetate (δ-76.33). The reaction mixture is cooled in a dry ice acetone bath and filtered to give 4.6 g (10.8%) of the cis isomer [17(a)], mp 132°–135° C. The THF filtrate is concentrated and the residue is triturated with 200 ml of petroleum ether and filtered to give 22 g of a solid which contains cis isomer [17(a)] and ammonium salt of ethyl trifluoroacetoacetate. This solid is washed with water to give an additional 7.0 g (16.5%) of cis isomer, mp 132°–135° C. The petroleum ether filtrate is further concentrated and cooled to give a third crop 7.0 g (16.5%), mp 89°–92° C., which is identified as the trans isomer (17b) by a single crystal X-ray analysis.

Anal. Calc'd. for $C_{15}H_{21}F_6N_1O_6$: C, 42.36; H, 4.98; N, 3.29; Found: C, 42.11: H, 5.03; N, 3.09.

An additional 4.0 g (9.4%) of a solid containing a mixture of cis and trans isomers is obtained by further concentration and cooling of the petroleum ether filtrate. The total yield of the cis and trans isomers is 53%.

(c)

Preparation of 3,5-Piperidine Dicarboxylic Acid, 2,6-bis(Trifluoromethyl)-2,6-Dihydroxy-4-Ethyl, Diethyl Ester A mixture of 368 g (2.0 mol) of ethyl trifluoroacetoacetate, 58 g (1.0 mol) of propionaldehyde and 1 ml of piperidine in 400 ml of $CH_2Cl_2$ is stirred for 1 hour at 20° C., then 1 hour at 50° C. and finally is refluxed for 1 hour. An additional 16.0 g (0.289 mol) of propionaldehyde is then added to the above mixture and the mixture is held at reflux for 2 hours. The heating mantle is removed. To the reaction mixture is passed 108 g (6.35 mol) of ammonia gas in 2 hours. The $^{19}F$ nmr indicates the reaction mixture contains 77% pure mixture (2:1) of cis isomer and trans isomer.

EXAMPLE 23

Preparation of 3,5-Piperidinedicarboxylic Acid, 2,6-Dihydroxy-4-(2-Methylpropyl)-2,6-bis(Trifluoromethyl)-, Diethyl Ester To a 1-liter single necked flask is charged 160 g (0.3524 mol) of the product of Example 2 and about 250 ml of ethanol. To this is slowly added 31.94 g (0.5286 mol) of 58% ammonium hydroxide. The flask is fitted with a condenser and a nitrogen line. The mixture is heated to reflux. After refluxing for 2 hours the material is cooled, concentrated and crystals are collected. Mother liquor yields a second crop. Total product yield is 34.16 g (21%) of solid; mp 69°–73° C.

Anal. Calc'd. $C_{17}H_{25}F_6N_1O_6$: C, 45.03; H, 5.51; N, 3.09; Found: C, 45.20; H, 5.50; N, 3.

This compound having the 2-methylpropyl at the 4-position is a preferred compound of the invention which is also useful as a precursor for particularly effective pyridine herbicides.

EXAMPLE 24

Preparation of 3,5-Piperidinedicarboxylic Acid, 4-Butyl-2,6-Dihydroxy-2,6-bis(Trifluoromethyl)-, Diethyl Ester To a 500 ml 3-necked flask is charged 40 g (0.0881 mol) of the product of Example 5 and about 200–250 ml of tetrahydrofuran. The flask is fitted with 2 dry ice condensers and a nitrogen inlet. Ammonia gas, 5 g (0.294 mol) is bubbled into the solution and the solution is stirred for 18 hours. The organics are concentrated, diluted with ethyl ether, washed in water, and dried on anhydrous $MgSO_4$. Traces of solvent are removed by vacuum pump. The residue is triturated with n-hexane and filtered to give 7.57 g (19%) of product, mp 77°–80° C.

Anal. Calc'd. for $C_{17}H_{25}F_6N_1O_6$: C, 45.03; H, 5.51; N, 3.09; Found: C, 44.96; H, 5.58; N, 3.03.

EXAMPLE 25

Preparation of 3,5-Piperidinedicarboxylic Acid, 1,4-Dihydro-2,6-bis(Trifluoromethyl)-2,6-Dihydroxy-4-(1-methylethyl), Diethyl Ester A 500 ml flask is charged with 150–200 ml of ethanol and 15.90 g (0.03613 mol) of the product of Example 8. The mixture is stirred while cooling in an ice bath. Cautiously, 3.24 g (0.05420 mol) of ammonium hydroxide is added to the mixture and stirring continued for 18 hours. The crude material is concentrated, stirred with n-hexane and placed in ice and filtered. Weight of the final product is 2.16 g (13.61%), mp 85°–89° C.

Anal. Calc'd. for $C_{16}H_{23}O_6N_1F_6$: C, 43.74; H, 5.28; N, 3.18;
Found: C, 44.08; H, 5.13; N, 2.74.

EXAMPLE 26

Preparation of 3,5-Piperidinedicarboxylic Acid, 2,6-Dihydroxy-4-Propyl-2,6-bis(Trifluoromethyl)-, Diethyl Ester A 500 ml round bottomed flask is charged with 150–200 ml of ethanol and 40 g (0.0909 mol) of the product of Example 9. The mixture is stirred by magnetic stirrer while 8.23 g (0.1363 mol) of 58% agueous ammonium hydroxide is added slowly to the flask. The mixture is stirred for 18 hours under nitrogen. The precipitate is filtered to yield 17.83 g (44.68%) of product, mp 140°–142° C.

Anal. Calc'd. for $C_{16}H_{23}O_6N_1F_6$: C, 43.73; H, 5.23; N, 3.18; Found: C, 43.67; H, 5.26; N, 3.19.

EXAMPLE 27

Preparation of 3,5-Piperidinedicarboxylic Acid,-2,6-Dihyroxy-2,6-bis(Trifluoromethyl)-4-[2-(5-Methylfuryl)]-, Diethyl Ester A 500 ml flask is charged with 25 g (0.2272 mol) of 5-methylfurfural, 83.67 g (0.4545 mol) of ethyl trifluoroacetoacetate and 150–200 ml of ethanol. The reaction mixture is stirred while 20.58 g (0.3408 mol) of 58% aqueous ammonium hydroxide is added. The mixture refluxes 5 hours and is cooled. The solvent is stripped and after standing for approximately 18 hours, crystallization begins. The product (recrystallized from hot n-hexane) gives 33.46 g product (30.87%) mp 98°–101° C.

Anal. Calc'd. for $C_{18}H_{21}F_6N_1O_6$: C, 45.28; H, 4.40; N, 2.93; Found: C, 45.50; H, 4.46; N, 2.92.

EXAMPLE 28

Preparation of 3,5-Piperidinedicarboxylic Acid, 2,6-Dihydroxy-2,6-bis(pentafluoroethyl)-4-Methyl-, Diethyl Ester A 3-necked 250 ml flask was charged with 60 ml of ethanol and 7.9 g (0.0154 mol) of diethyl 2,6-bis(pentafluoroethyl)-2,6-dihydroxy-4-methyltetrahydropyran-3,5-dicarboxylate. The solution is cooled before adding 1.39 g (0.0231 mol) of 58% aqueous ammonium hydroxide by pipette. The mixture is stirred for 18 hours at room temperature. The mixture is concentrated and the residue is triturated with n-hexane to yield 2.7 g (35%) of crystals, mp 128°–130° C.

Anal. Calc'd. for $C_{16}H_{19}O_6N_1F_{10}$: C, 37.57; H, 3.71; N, 2.73; Found: C, 37.72; H, 3.75; N, 2.56.

EXAMPLE 29

Preparation of 3,5-Piperidinedicarboxylic. Acid, 4-(2-Furyl)-2,6-Dihydroxy-2,6-bis(Trifluoromethyl)-, Diethyl Ester A 500 ml 3-necked flask is charged with 6 ml ethanol, 29.07 g (0.3 mol) of 2-furaldehyde and 0.46 g (0.6 mol) of ethyl trifluoroacetoacetate. The reaction mixture is cooled in an ice bath before 21.15 g (0.35 mol) of 58% aqueous ammonium hydroxide is added slowly and allowed to stir. The mixture is heated at reflux for 2 hours and cooled. The resulting precipitate is filtered and recrystallized from hot ethanol to provide 53.34 g of crystals (39%) mp 129°–131° C.

Anal. Calc'd. for $C_{17}H_{17}F_6N_1O_7$: C, 44.06; H, 4.10; N, 3.02;

Found: C, 44.04; H, 4.12; N, 3.03.

EXAMPLE 30

Preparation of 3,5-Piperidinedicarboxylic Acid, 2,6-Dihydroxy-4-(2-Thienyl)-2,6-bis(Trifluoromethyl)-, Diethyl Ester A 3-necked flask is charged with 60 ml of ethanol, 33.64 g (0.3 mol) of 2-thiophenecarboxaldehyde and 110.46 g (0.6 mol) of ethyl trifluoroacetoacetate. The resulting mixture is stirred and cooled in an ice water bath before 21.15 g (0.35 mol) of 58% aqueous ammonium hydroxide was slowly added. The reaction mixture is refluxed for 3 hours and is cooled. The solid mixture is filtered and is recrystallized from methyl cyclohexane to give 81.70 g of product (57%) mp 103°–105° C.

Anal. Calc'd. for $C_{17}H_{19}F_6N_1O_6S$: C, 42.58; H, 3.96; N, 2.92; S, 6.68; Found: C, 43.08; H, 4.06; N, 2.78; S, 6.44.

Additional compounds of this invention were prepared in a procedure similar to Example 17(b) or similar to the procedure of Example 17(c) and are described in Table II below.

As noted above, the compounds of this invention have been found to be effective as pre-emergent herbicides. Tables I and II summarize results of tests conducted to determine the pre-emergent herbicidal activity of the compounds of this invention.

The pre-emergent tests are conducted as follows:

A good grade of top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable powder suspension and the soil are thoroughly mixed, and used as a cover layer for prepared pans. After treatment, the pans are moved into a greenhouse bench where they are watered from below as needed to give adequate moisture for germination and growth.

Approximately 2–3 weeks after seeding and treating, the plants are observed and the results recorded. Table III below summarizes such results. The herbicidal rating is obtained by means of a fixed scale based on the percent injury of each plant species. The ratings are defined as follows:

| % Inhibition | Rating |
|---|---|
| 0–24 | 0 |
| 25–49 | 1 |
| 50–74 | 2 |
| 75–100 | 3 |

The plant species utilized in one set of tests, the data for which are shown in Table III, are identified by letter in accordance with the following legend:

| | | |
|---|---|---|
| A-Canada Thistle* | E-Lambsquarters | I-Johnsongrass* |
| B-Cocklebur | F-Smartweed | J-Downy Brome |
| C-Velvetleaf | G-Yellow Nutsedge* | K-Barnyardgrass |
| D-Morningglory | H-Quackgrass* | |

*Grown from vegetative propagules

TABLE II

PREPARATION OF 3,5 PIPERIDINE DICARBOXYLIC ACID, 2,6-BIS(FLUOROALKYL)-2,6 DIHYDROXY-4-ALKYL, DIESTERS

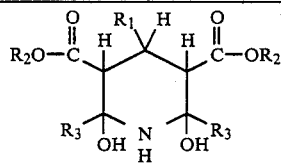

| Example Number | $R_1$ | $R_2$ | $R_3$ | Analysis C Calc'd | C Found | H Calc'd | H Found | N Calc'd | N Found | Melting Point °C. | Isomer % Ratio Cis | Trans |
|---|---|---|---|---|---|---|---|---|---|---|---|---|
| 31 | —$CH_2CH(CH_3)_2$ | $CH_3$ | $CF_3$ | 42.36 | 42.84 | 5.00 | 4.94 | 3.29 | 3.29 | 102–106 | 100 | — |
| 32 | —$CH_2CH(CH_3)_2$ | $CH_2CH_3$ | $CF_2H$ | 48.92 | 48.93 | 6.52 | 6.51 | 3.36 | 3.31 | 98–100 | — | 100 |
| 33 | —$C_2H_4OC_2H_5$ | $CH_2CH_3$ | $CF_3$ | 40.73 | 40.69 | 4.56 | 4.72 | 2.98 | 3.14 | $n_D^{25} = 1.4269$ | 58 | 42 |
| 34 | —$CH_2OCH_3$ | $CH_2CH_3$ | $CF_3$ | 40.82 | 40.87 | 4.80 | 4.70 | 3.17 | 3.40 | 122–123 | — | — |
| 35 | —$C_2H_4SCH_3$ | $CH_2CH_3$ | $CF_3$ | 40.76 | 40.81 | 4.92 | 4.86 | 2.97 | 3.10 | 53–73 | 88 | 12 |
| 36 | —$CH_2O$ | $CH_2CH_3$ | $CF_3$ | 48.75 | 48.74 | 4.87 | 4.87 | 2.71 | 2.71 | 102–109 | — | — |

TABLE III

| Compound of Example No. | Kg/ha | Pre-Emergent A | B | C | D | E | F | G | H | I | J | K |
|---|---|---|---|---|---|---|---|---|---|---|---|---|
| 1 | 11.2 | — | 0 | 0 | 0 | 2 | 0 | 0 | 1 | 1 | — | 3 |
| 2 | 11.2 | — | 0 | 3 | 2 | 3 | 3 | 0 | 0 | 0 | 3 | 3 |

TABLE III-continued

| Compound of Example No. | Kg/ha | Pre-Emergent | | | | | | | | | | |
|---|---|---|---|---|---|---|---|---|---|---|---|---|
| | | A | B | C | D | E | F | G | H | I | J | K |
| 3 | 11.2 | 0 | 0 | 0 | 0 | 2 | 0 | 0 | 0 | 0 | 1 | 2 |
| 4 | 11.2 | 3 | 0 | 0 | 0 | 1 | 0 | 0 | 0 | 0 | 0 | 2 |
| 5 | 11.2 | 0 | 0 | 3 | 3 | 3 | 3 | 0 | 0 | 0 | 3 | 3 |
| 6 | 11.2 | 0 | 0 | 3 | 2 | 3 | 3 | 0 | 0 | 0 | 0 | 3 |
| 7 | 11.2 | 0 | 0 | 0 | 1 | 0 | 0 | 0 | 0 | 0 | 0 | 1 |
| 8 | 11.2 | 0 | 0 | 0 | 0 | 3 | 3 | 0 | 0 | 0 | 1 | 3 |
| 9 | 11.2 | 1 | 0 | 2 | 3 | 3 | 3 | 0 | 0 | 0 | 1 | 3 |
| 10 | 11.2 | 3 | 0 | 0 | 0 | 0 | 0 | 0 | 0 | 0 | 1 | 2 |
| 11 | 11.2 | 0 | 0 | 0 | 0 | 1 | 0 | 0 | 0 | 0 | 0 | 0 |
| 12 | 11.2 | 0 | 0 | 0 | 0 | 0 | 0 | 0 | 0 | 0 | 0 | 3 |
| 13 | 11.2 | 0 | 0 | 0 | 3 | 0 | — | 0 | 0 | 0 | 0 | 3 |
| 14 | 11.2 | 0 | 0 | 0 | 0 | 0 | 0 | 0 | 0 | 0 | 0 | 3 |
| 15 | 11.2 | 0 | 0 | 0 | 0 | 0 | 0 | 0 | 0 | 0 | 0 | 0 |
| 16 | 11.2 | 0 | 1 | 0 | 0 | 3 | 3 | 0 | 0 | 0 | 0 | 3 |
| 17 | 11.2 | 0 | 0 | 0 | 3 | 1 | 1 | 0 | 0 | 0 | 0 | 3 |
| 18 | 11.2 | 0 | 0 | 0 | 0 | 0 | — | 0 | 0 | 0 | 0 | 0 |
| 19 | 11.2 | 1 | 2 | 1 | 3 | 3 | — | 3 | 3 | 0 | 1 | 3 |
| 20 | 11.2 | 0 | 0 | 0 | 0 | 0 | 0 | 0 | 0 | 0 | 0 | 1 |
| 22(a) | 11.2 | 3 | 0 | 0 | 0 | 3 | 3 | 0 | 0 | 0 | 2 | 3 |
| 22(b) | 11.2 | 0 | 0 | 0 | 0 | 1 | 0 | 0 | 0 | 0 | 0 | 1 |
| 23 | 11.2 | — | 0 | 1 | 0 | 3 | 0 | 0 | 3 | 0 | 1 | 3 |
| 24 | 11.2 | — | 0 | 2 | 2 | 3 | 2 | 0 | 2 | 3 | 3 | 3 |
| 25 | 11.2 | 2 | 0 | 2 | 0 | 2 | 2 | 0 | 0 | 0 | 2 | 3 |
| 26 | 11.2 | 1 | 0 | 0 | 0 | 3 | 2 | 0 | 0 | 1 | 1 | 3 |
| 27 | 11.2 | 0 | 0 | 0 | 0 | 2 | 0 | 0 | 0 | 0 | 0 | 3 |
| 28 | 11.2 | 0 | 0 | 0 | 1 | 3 | 0 | 0 | 0 | 0 | 3 | 0 |
| 29 | 11.2 | — | 0 | 0 | 0 | 1 | 0 | 0 | 0 | 0 | 0 | 0 |
| 30 | 11.2 | — | 0 | 0 | 0 | 3 | 0 | 0 | 0 | 0 | 0 | 0 |
| 31 | 11.2 | 0 | 0 | 3 | 2 | 3 | — | 0 | 0 | 0 | 3 | 3 |
| 32 | 11.2 | 0 | 0 | 0 | 1 | 1 | — | 0 | 0 | 0 | 0 | 3 |
| 33 | 11.2 | 0 | 0 | 1 | 1 | 2 | — | 0 | 0 | 3 | 1 | 2 |
| 34 | 11.2 | 3 | 0 | 2 | 2 | 3 | — | 0 | 0 | 0 | 1 | 3 |
| 35 | 11.2 | 1 | 0 | 0 | 0 | 1 | — | 1 | 0 | 0 | 1 | 3 |
| 36 | 11.2 | — | 0 | 0 | 0 | 0 | 0 | 0 | 0 | 0 | 0 | 0 |

The compounds were further tested by utilizing the above procedure on the following plant species:

| L | Soybean | R | Hemp Sesbania |
|---|---|---|---|
| M | Sugarbeet | E | Lambsquarters |
| N | Wheat | F | Smartweed |
| O | Rice | C | Velvetleaf |
| P | Sorghum | J | Downy Brome |
| B | Cocklebur | S | Panicum |
| Q | Wild Buckwheat | K | Barnyardgrass |
| D | Morningglory | T | Crabgrass |

The results are summarized in Table IV below.

TABLE IV

| Compound of Example No. | Kg/ha | Pre-Emergent | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 1 | 5.6 | 0 | 2 | 1 | 1 | 0 | 0 | 0 | 1 | 0 | 1 | 0 | 0 | 1 | 1 | 2 | 3 |
| 2 | 5.6 | 1 | 3 | 0 | 2 | 2 | 0 | 3 | 1 | 1 | 3 | 2 | 1 | 0 | 2 | 2 | 2 |
| | 1.12 | 1 | 2 | 0 | 1 | 0 | 0 | 3 | 0 | 1 | 2 | 1 | 1 | 0 | 1 | 2 | 2 |
| | .274 | 0 | 1 | 0 | 0 | 0 | 3 | 0 | 0 | 1 | 0 | 0 | 0 | 0 | 0 | 0 | 1 |
| 5 | 5.6 | 0 | 3 | 0 | 1 | 0 | 0 | 3 | 2 | 1 | 3 | 3 | 2 | 0 | 3 | 3 | 3 |
| 6 | 5.6 | 2 | 3 | 2 | 2 | 1 | 0 | 3 | 3 | 2 | 3 | 3 | 3 | 1 | 3 | 3 | 3 |
| 8 | 5.6 | 0 | 2 | 0 | 1 | 0 | 0 | 2 | 1 | 1 | 3 | 1 | 2 | 2 | 3 | 3 | 3 |
| | 1.12 | 1 | 1 | 0 | 0 | 0 | 0 | 1 | 0 | 0 | 0 | 0 | 0 | 0 | 0 | 1 | 1 |
| 9 | 5.6 | 1 | 3 | 1 | 1 | 0 | 0 | 3 | 2 | 2 | 3 | 2 | 3 | 1 | 2 | 3 | 3 |
| | 1.12 | 0 | 0 | 1 | 0 | 0 | 0 | 1 | 0 | 2 | 0 | 0 | 0 | 1 | 0 | 0 | 0 |
| 13 | 5.6 | 0 | 0 | 0 | 0 | 0 | 0 | 0 | 0 | 0 | 0 | — | 0 | 0 | 0 | 1 | 1 |
| 17(a) | 5.6 | 1 | 3 | 0 | 0 | 1 | 0 | 3 | 0 | 1 | 1 | 3 | 0 | 3 | 3 | 3 | 1 |
| | 1.12 | 0 | 0 | 0 | 0 | 0 | 0 | 0 | 0 | 0 | 2 | 3 | 0 | 1 | 0 | 0 | 1 |
| | .274 | 0 | 0 | 0 | 0 | 0 | 0 | 0 | 0 | 0 | 0 | 3 | 0 | 0 | 0 | 0 | 0 |
| 18 | 5.6 | 0 | 1 | 0 | 0 | 0 | 0 | 0 | 2 | 0 | 0 | 0 | 0 | 0 | 0 | 2 | 3 | 1 |
| | 1.12 | 1 | 1 | 0 | 0 | 0 | 0 | 0 | 0 | 0 | 0 | 0 | 0 | 0 | 0 | 0 | 0 |
| 19 | 5.6 | 0 | 2 | 1 | 1 | 0 | 0 | 1 | 1 | 0 | 2 | 1 | 0 | 1 | 2 | 3 | 3 |
| | 1.12 | 0 | 1 | 0 | 0 | 0 | 0 | 0 | 0 | 0 | 0 | 0 | 0 | 0 | 0 | 2 | 2 |
| | .274 | 0 | 0 | 0 | 0 | 0 | 0 | 0 | 0 | 0 | 0 | 0 | 0 | 0 | 0 | 0 | 2 |
| 20 | 5.6 | 0 | 2 | 0 | 1 | 0 | 0 | 1 | 2 | 1 | 2 | 2 | 1 | 1 | 2 | 3 | 3 |
| | 1.12 | 0 | 1 | 0 | 0 | 0 | 0 | 0 | 0 | 2 | 0 | 0 | 0 | 0 | 0 | 0 | 1 |
| 21 | 5.6 | 2 | 2 | 0 | 0 | 0 | 0 | 2 | 1 | 0 | 2 | 2 | 0 | 1 | 2 | 3 | 3 |
| | 1.12 | 0 | 1 | 0 | 0 | 0 | 0 | 0 | 0 | 0 | 3 | 0 | 0 | 0 | 0 | 2 | 2 |
| 22 | 5.6 | 0 | 0 | 0 | 0 | 0 | 0 | 0 | 0 | 0 | 2 | — | 0 | 0 | 0 | 2 | 0 |
| 26 | 5.6 | 0 | 1 | 0 | 0 | 0 | 0 | 0 | 0 | 0 | 0 | — | 0 | 0 | 2 | 3 | 2 |
| | 1.12 | 0 | 1 | 0 | 0 | 0 | 0 | 0 | 0 | 0 | 0 | — | 0 | 0 | 1 | 2 | 1 |
| | .274 | 0 | 0 | 0 | 0 | 0 | 0 | 0 | 0 | 0 | 0 | — | 0 | 0 | 0 | 1 | 0 |

TABLE IV-continued

| Compound of Example No. | Kg/ha | Pre-Emergent | | | | | | | | | | | | | | |
|---|---|---|---|---|---|---|---|---|---|---|---|---|---|---|---|---|
| | | L | M | N | O | P | B | Q | D | R | E | F | C | J | S | K | T |
| 27 | 5.6 | 0 | 0 | 0 | 0 | 0 | 0 | 0 | 0 | 0 | 0 | — | 0 | 0 | 0 | 2 | 1 |

The compounds of this invention may be incorporated into herbicidal compositions using commonly-known techniques. It is expected that the herbicidal compositions of this invention including concentrates which require dilution prior to application may typically contain at least one active ingredient and an adjuvant in liquid or solid form. Such compositions are prepared by admixing the active ingredient with an adjuvant including diluents, extenders, carriers, and conditioning agents to provide compositions in the form of finely-divided particulate solids, granules, pellets, solutions, dispersions, or emulsions. Thus the active ingredient can be used with an adjuvant such as a finely-divided solid, a liquid of organic origin, water, a wetting agent, a dispersing agent, an emulsifying agent, or any suitable combination of these.

It is believed that the compositions of this invention, particularly liquids and wettable powders, should preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and non-ionic agents can be used with equal facility.

Typical wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powder compositions of this invention usually contain from about 0.5 to 80 parts (preferably as high as possible up to 80 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient, a suitable nonaqueous solvent therefor, and an emulsification agent until uniform and then homogenizing to give a stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% (preferably as high as possible) by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons, and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners, and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium Ureas N'-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea Carbamates/Thiolcarbamates 2-Chloroallyl diethyldithiolcarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
Ethyl N,N-dipropylthiolcarbamate
S-propyl dipropylthiolcarbamate Acetamides/Acetanilides/Anilines/Amides 2-Chloro-N,N-diallylacetamide
N,N-dimethyl-2,2-diphenylacetamide
N-(2,4-dimethyl5-[[(trifluoromethyl)sulfonyl]amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
$\alpha,60,\alpha$-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl) glycine and its salts Ethers 2,4-Dichlorophenyl-4-nitrophenyl ether
2-Chloro-$\alpha,\alpha,\alpha$-trifluoro-p-tolyl-3-ethoxy-4-nitrodiphenyl ether Miscellaneous 2,6-Dichlorobenzonitrile
Monosodium acid methanearsonate
Disodium methanearsonate Fertilizers useful in combination with the active ingredients include, for example, ammonium nitrate, urea, potash, and superphosphate. Other useful additaments include materials in which plant organisms take root and grow such as compost, manure, humus, sand and the like.

Typical herbicidal formulations of the types described above are set out in several illustrative embodiments below.

| | | Weight Percent |
|---|---|---|
| I. Emulsifiable Concentrates | | |
| A. | Compound of Example No. 5 | 1.0 |
| | Free acid of complex organic phosphate of aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 86.96 |
| | | 100.00 |
| B. | Compound of Example No. 16 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |
| II. Flowables | | |
| A. | Compound of Example No. 6 | 25.0 |
| | Methyl cellulose | 0.3 |
| | Silica aerogel | 1.5 |
| | Sodium lignosulfonate | 3.5 |
| | Sodium N—methyl-N—oleyl taurate | 2.0 |
| | Water | 67.7 |
| | | 100.0 |
| B. | Compound of Example No. 17 | 45.0 |
| | Methyl cellulose | .3 |
| | Silica aerogel | 1.5 |
| | Sodium lignosulfonate | 3.5 |
| | Sodium N—methyl-N—oleyl taurate | 2.0 |
| | Water | 47.7 |
| | | 100.0 |
| III. Wettable Powders | | |
| A. | Compound of Example No. 5 | 25.0 |
| | Sodium lignosulfonate | 3.0 |
| | Sodium N—methyl-N—oleyl-taurate | 1.0 |
| | Amorphous silica (synthetic) | 71.0 |
| | | 100.0 |
| B. | Compound of Example No. 21 | 80.0 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 6 | 10.0 |
| | Sodium lignosulfonate | 3.0 |
| | Sodium N—methyl-N—oleyl-taurate | 1.0 |
| | Kaolinite clay | 86.0 |
| | | 100.0 |
| IV. Water-Soluble Powders | | |
| A. | Compound of Example No. 1 | 10.0 |
| | Sodium dioctyl sulfocuccinate | 2.0 |
| | Silica aerogel | 5.0 |
| | Methyl violet | 0.1 |
| | Sodium bicarbonate | 82.9 |
| | | 100.0 |
| B. | Compound of Example No. 17 | 90.0 |
| | Ammonium phosphate | 10.00 |
| | | 100.00 |
| V. Dusts | | |

| | Weight Percent |
|---|---|
| A. Componnd of Example No. 2 | 2.0 |
| Attapulgite | 98.0 |
| | 100.0 |
| B. Compound of Example No. 9 | 60.0 |
| Montmorillonite | 40.0 |
| | 100.0 |
| C. Compound of Example No. 13 | 30.0 |
| Ethylene glycol | 1.0 |
| Bentonite | 69.0 |
| | 100.0 |
| D. Compound of Example No. 16 | 1.0 |
| Diatomaceous earth | 99.0 |
| | 100.0 |
| VI. Granules | |
| A. Compound of Example No. 8 | 15.0 |
| Granular attapulgite (20/40 mesh) | 85.0 |
| | 100.0 |
| B. Compound of Example No. 9 | 30.0 |
| Diatomaceous earth (20/40) | 70.0 |
| | 100.0 |
| C. Compound of Example No. 26 | 1.0 |
| Ethylene glycol | 5.0 |
| Methylene blue | 0.1 |
| Pyrophyllite | 93.9 |
| | 100.0 |
| D. Compound of Example No. 19 | 5.0 |
| Pyrophyllite (20/40) | 95.0 |
| | 100.0 |

When operating in accordance with the present invention, effective amounts of the compounds of this invention are applied to the soil or plant locus containing the plants in any convenient fashion. The application of liquid and particulate solid compositions to the soil can be carried out by conventional methods, e.g., power dusters, boom and hand sprayers, and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective pre-emergence application to the plants or to the soil a dosage of from 0.02 to about 11.2 kg/ha, preferably from about 0.1 to about 5.60 kg/ha of herbicide is usually employed. Lower or higher rates may be required in some instances. One skilled in the art can readily determine from this specification, including the above examples, from the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations except to the extent indicated in the following claims.

I claim:

1. An herbicidal composition comprising an adjuvant and a herbicidally effective amount of a compound of the formula

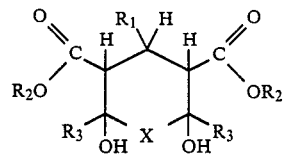

wherein X is O, $R_1$ is selected from the group consisting of hydrogen, lower alkyl, phenyl, phenylmethyl, loweralkoxy loweralkyl, loweralkylthio loweralkyl, cycloloweralkyl and heterocyclic radicals selected from 2-thienyl, 3-thienyl, 2-furyl and 3-furyl; $R_2$ is $C_{1-4}$ alkyl radical and $R_3$ represents a $C_{1-4}$ fluoroalkyl radical provided that when $R_3$ is pentafluoroethyl, $R_1$ cannot be hydrogen, cycloloweralkyl, or 1-methylethyl.

2. Compositions of claim 1 wherein $R_1$ is alkyl, $C_{1-5}$.
3. Compositions of claim 2 wherein $R_1$ is alkyl, $C_{2-4}$.
4. Composition of claim 3 wherein $R_3$ is a trifluoromethyl radical.
5. Composition of claim 1 wherein $R_1$ is a butyl radical.
6. Composition of claim 1 wherein $R_1$ is a 2-methylpropyl.
7. Composition of claim 1 wherein $R_1$ is a propyl radical.
8. Composition of claim 1 wherein $R_3$ is trifluoromethyl.
9. The composition of claim 1 wherein $R_1$ is ethyl.
10. The composition of claim 1 wherein $R_3$ is difluoromethyl.
11. A method for controlling undesirable plants which comprises applying to the locus thereof a herbicidally effective amount of a compound having the formula

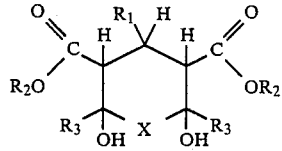

wherein X is O, $R_1$ is selected from the group consisting of hydrogen, lower alkyl, phenyl, phenylmethyl, loweralkoxyloweralkyl, loweralkylthioloweralkyl, cycloloweralkyl and heterocyclic radicals selected from 2-thienyl, 3-thienyl, 2-furyl and 3-furyl; $R_2$ is $C_{1-4}$ alkyl radical and $R_3$ represents a $C_{1-4}$ fluoroalkyl radical provided that when X is O and $R_3$ is pentafluoroethyl, $R_1$ cannot be hydrogen, cycloweralkyl, or 1-methylethyl.

12. Method of claim 11 wherein $R_1$ is alkyl, $C_{1-5}$.
13. Method of claim 12 wherein $R_1$ is alkyl, $C_{2-4}$.
14. Method of claim 13 wherein $R_3$ is a trifluoromethyl radical.
15. Method of claim 11 wherein $R_1$ is a butyl radical.
16. Method of claim 11 wherein $R_1$ is 2-methylpropyl.
17. Method of claim 11 wherein $R_1$ is a propyl radical.
18. Method of claim 11 wherein $R_3$ is trifluoromethyl.
19. Method of claim 11 wherein $R_1$ is ethyl.
20. The method of claim 11 wherein $R_3$ is difluoromethyl.
21. A compound of the formula

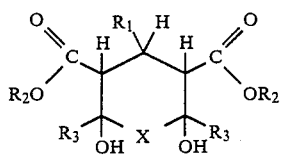

wherein $R_1$ is selected from branched-chain lower alkyl, loweralkoxyloweralkyl, loweralkylthioloweralkyl, cycloloweralkyl, and cycloloweralkanylloweralkyl radicals, $R_2$ is a $C_{1-4}$ alkyl radical and $R_3$ represents a $C_{1-4}$ fluoroalkyl radical.

22. A compound according to claim 21 wherein $R_1$ is 2-methylpropyl.

23. A compound according to claim 22 wherein $R_3$ is trifluoromethyl.

* * * * *